United States Patent [19]
Gray

[11] Patent Number: 5,792,208
[45] Date of Patent: Aug. 11, 1998

[54] HEART PACEMAKER

[76] Inventor: Noel Domond Gray, No. 10, The Cove, Forster Keys N.S.W. 2428, Australia

[21] Appl. No.: 885,706

[22] Filed: Jun. 30, 1997

Related U.S. Application Data

[62] Division of Ser. No. 424,401, filed as PCT/AU93/00541, Oct. 20, 1993, Pat. No. 5,674,259 continuation-in-part of PCT/AU92/00219, May 15, 1992..

[30] Foreign Application Priority Data

Oct. 20, 1992 [AU] Australia ............... PL5397

[51] Int. Cl.$^6$ .................... A61N 1/375
[52] U.S. Cl. ............ 607/36; 607/20; 607/129; 607/148
[58] Field of Search ........ 607/36, 9, 129–131, 607/148, 119, 4, 17, 19, 20

[56] References Cited

U.S. PATENT DOCUMENTS

| | | |
|---|---|---|
| 3,572,345 | 3/1971 | Auphan . |
| 3,593,718 | 7/1971 | Krasner et al. . |
| 4,030,509 | 6/1977 | Hellman et al. . |
| 4,256,115 | 3/1981 | Bilitch . |
| 4,458,677 | 7/1984 | McCorkle, Jr. . |
| 4,475,551 | 10/1984 | Lauger et al. . |
| 4,770,177 | 9/1988 | Schroeppel . |
| 4,791,931 | 12/1988 | Slate . |
| 4,928,688 | 5/1990 | Mower . |
| 5,097,833 | 3/1992 | Campos . |
| 5,224,476 | 7/1993 | Ideker et al. . |

FOREIGN PATENT DOCUMENTS

| | | |
|---|---|---|
| 226164 | 12/1966 | European Pat. Off. . |
| 507325 | 3/1976 | U.S.S.R. . |
| 760981 | 9/1980 | U.S.S.R. . |
| 848038 | 7/1981 | U.S.S.R. . |
| WO88./03424 | 5/1988 | WIPO . |
| WO91/08021 | 6/1991 | WIPO . |

*Primary Examiner*—Jeffrey R. Jastrzab
*Attorney, Agent, or Firm*—Rockey, Milnamow & Katz, Ltd.

[57] ABSTRACT

A heart pacemaker which is arranged to stimulate the apical area of the heart. Stimulation of this area provides synchronous mechanical contraction of the left and right ventricles and overcomes the problem of pacemaker induced left bundle branch block type conduction disturbance. The pacemaker has a base surface which conforms to the apical area of the heart and mounts a plurality of epicardial stimulating electrodes. Selection of electrodes can be made to provide the most clinically appropriate stimulation. An opposite side of the pacemaker is arranged to contact the diaphragm and is proved with sensing electrodes to sense activity of the diaphragm and adjust pacing of the heart in accordance with changes in physical activity of the patient. The electrodes used are preferably of capacitive construction, having first and second capacitive plates either side of a dielectric formed by he body of the pacemaker.

6 Claims, 7 Drawing Sheets

HEART PACEMAKER

CROSS REFERENCE TO RELATED APPLICATIONS

This application is a division of U.S. patent application Ser. No. 08/424,401 now U.S. Pat. No. 5,674,259 filed Jun. 15, 1995, under 35 U.S.C. §371 from PCT International Patent Application No. PCT/AU93/00541 having an international filing date of 20 Oct. 1993 (20.10.93) and claiming the priority of Australian Patent Application No. PL 5397, which has a filing date of 20 Oct. 1992 (20.10.92). U.S. patent application Ser. No. 08/424,401 also is a continuation-in-part of PCT International Patent Application No. PCT/AU92/00219 having an International Filing Date of 15 May 1992 (15.05.92) and claiming the priority of Australian Patent Application No. PK 6207, which has a filing date of 17 May 1991 (17.05.91).

BACKGROUND OF THE INVENTION

1. Field of the Invention

The present invention relates to a heart pacemaker.

2. Description of the Prior Art

An existing cardiac pacemaker consists of a power source and electronic circuitry which together constitute a pulse generator housed within an hermetically sealed metal capsule. The metal capsule is arranged to be inserted within a patients body normally near one of the pectoral muscles. An insulated lead having its proximal end connected into a receiving port of the metal capsule so as to provide a direct connection with the pulse generator, has its distal end connected to one or more bare metal electrodes which are located inside the patients heart. Typically, such transvenous electrodes are positioned in the right ventricle and deliver stimulating impulses to the endocardium. This was first successfully performed by Lagergren et al at the Karolinska Institute in Stockholm Sweden 1962. Prior to this the stimulating electrodes were attached to the epicardium by thoracotomy for both external and implantable pacemakers.

Transvenous electrodes suffer from a number of problems one of which is a loss of synchronous mechanical contraction of the left and right ventricles. This is referred to as pacemaker induced left branch block type conduction disturbance and is recognised by a lengthening of the QRS complex. The resultant reduction in left ventricular chamber performance is indicative of a reduced cardiac output, especially at higher heart rates as with rate responsive physiological pacemakers. The cause of the pacemaker induced left bundle branch block in the positioning of the stimulating electrode on the free wall of the right ventricle. This right ventricular pacing causes an intraventricular delay in the transmission of stimulating impulses to the left ventricle. In a normal healthy heart the ventricles are stimulated to depolarisation by nerves that are found in both the left and the right ventricles, thus ensuring synchronous isovolumic systole occurs in both ventricles in every heart beat. The single transvenous electrode positioned in the right ventricle cannot replicate this process.

Conventional pacemakers using electrodes placed transvenous in the right ventricle of the heart also suffer from a number of other problems. Relatively long conductive leads are used to connect the implanted electrode to the pulse generator housed in the pacemaker body. There is thus a relatively large impedance between the pulse generator and the electrode, requiring the generation of higher voltages and resulting in a large drain on the power source. This shortens the life of the pacemaker.

It is necessary to surgically implant the electrode into the heart. This can be an expensive procedure, which in conventional transvenous electrodes, requires the provision of expensive equipment to perform fluroscopy for positioning of the electrode. The expense of the procedure limits application.

Further, generally only a single electrode is implanted. This single electrode is used both for sensing cardiac activity and providing pacing pulses. In pacing at higher rates, polarisation of the electrode site increases due to the reduced time between succeeding stimulating impulses thereby not permitting dispersion of the voltage of polarisation. Pacing voltage must therefore be increased to overcome the polarisation potential and apparent increase in impedance. This, again, results in an increased drain on the power source.

Further, coupling the sensing and pacing functions in a single electrode results in the possibility of local polarisation interfering with the sensing function.

Yet a further problem is movement of the electrode away from the original implantation side. This results in the incorrect stimulation of the cardiac tissue.

Further, an operation would be necessary to correct the electrode position. Positioning of the electrode when only a single electrode is used is very important. Any error can lead to problems.

A method of pacing both ventricles has been proposed by Mower (U.S. Pat. No. 4,928,688). The Mower device uses two transvenous electrodes, one positioned in the usual place in the right ventricle and a second electrode positioned in the coronary sinus about the left ventricle (derived from U.S. Pat. No. 4,458,677 to McCorkle). At least one ECG amplifier is arranged to separately detect contraction of each ventricle and a stimulator is then activated for issuing stimulating pulses to the electrodes in an attempt to assure a simultaneous contraction of both ventricles. The device is designed to restore substantially simultaneous contraction of both ventricles where there is a bundle branch block to either right or left ventricle or a slow conduction to either. It does not refer to correction of pacemaker imposed left bundle branch block and uses electrodes with the dual functions of sensing and stimulation. There is no disclosure of an arrangement for restoring a uniform spread of the depolarisation pattern at the heart as in nature. Instead, two foci of stimulation are employed, one in the right ventricle near the apex and the other high up the heart on the left ventricular of free wall. Further, the surgical procedure necessary to implant an electrode in the coronary sinus is complex and difficult. Furthermore, Mower provides no solution to the problems of using single electrodes connected by relatively long leads.

From a first aspect, the present invention provides a heart pacemaker, comprising a base member mounting a plurality of pacing electrodes, the base member being adapted to fit to the apex of the heart such that the pacing electrodes are positioned about the apex of the heart and able to provide stimulation to the apex of the heart, and pulse generator means for causing the electrodes to provide cardiac stimulating pulses to the apical area.

The base member preferably forms part of a hermetically sealed body comprising pulse generator circuitry and a power source for providing the pacing function. The entire body is preferably of such size that it can be placed at the apex of the heart in between the diaphragm and the heart. Surgical placement of such a device maybe a fairly simple procedure and can preferably be performed by today's endoscopic techniques.

The base member is preferably shaped to conform to the apical area of the heart so that electrodes on the surface of the pacemaker contact heart tissue. The base member preferably comprises a concave surface, the electrodes preferably being placed on the concave surface almost flush with the surface. The concave surface is preferably designed to "hug" the apical area.

The apex of the heart is where the free walls of left and right ventricles meet the intraventricular septum. The left ventricular apex is more prominent than that of the right ventricle at the apical area. By positioning the plurality of the electrodes about this apical area, the electrodes are preferably able to provide a depolarisation wave that spreads up and into the whole heart in an even fashion, in a sense mirroring the excitement pattern of a healthy heart. This will preferably result in both ventricles and the septum receiving a stimulating impulse substantially simultaneously. Substantially simultaneous mechanical activity of both ventricles can then occur with support from a rigid base formed by a stiffening of the intraventricular septum of the apex. This contractile pattern will preferably help to overcome compromises to hemodynamics associated with the asgnergic contractile pattern of left bundle branch block and the similar condition imposed by the conventional intraventricular pacemakers. Pulsing the apex of the left ventricle the apex of the left ventricle being more prominent of the apex of the heart than the apex of the right ventricle provides a hemodynamic advantage over conventional pacing.

The heart pacemaker of the present invention is preferably an epicardial extra-cardiac device, the electrodes contacting the surface of the heart tissue and not being implanted therein. Provision of a hermetically sealed body containing the pulse generator circuitry and power source and arranged to be placed next to the heart preferably does away with the need for long connecting leads as employed in conventional intracardiac pacemakers, such as disclosed in the Mower patent.

An array of electrodes is preferably provided on the surface of the base member. Preferably any number of the electrodes may be selected to provide pacing pulses, in order to provide the most clinically appropriate stimulation. Further, sensing electrodes are also preferably placed in an array and are preferably separate from the pacing electrodes.

Preferably, selection means are provided for selecting which sensing and/or pacing electrodes to use. The selection means may comprise an electrode multiplexer and control means for determining which electrodes are to be selected for sensing and/or pacing. Periodic selection re-selection of sensing/pacing electrodes may be carried out by telemetry. For example, a cardiac specialist utilising telemetry, may first of all apply a number of test pulses via selected electrodes to determine the most optimum electrodes to use to provide the most clinically appropriate stimulation. This "calibration" may be done on installation of the pacemaker and also at periodic intervals. Conventional pacemakers are calibrated (eg. pulse-width, pacemaker voltage, etc.) by telemetry and the selection process in accordance with the preferred embodiment of the present invention could also take place at this time.

A further option is that selection could be determined internally of the pacemaker by an appropriate programmed control means constantly monitoring cardiac response and having the facility to select any of the pacing/sensing electrodes to determine the best response.

Furthermore, a control means may control the selection means to switch constantly between preselected electrodes in order to reduce polarisation effects.

A further technique for reducing polarisation of the electrode area may also be applied. The polarity of pacing pulses may be reversed, either periodically or on alternate pulses. This technique is described in copending patent application PCT/AU92/00219, and the disclosure of that application is incorporated herein. Separation of the sensing electrodes from the pacing electrodes reduces possible polarisation effects on sensing electrodes.

Reduction of polarisation enables lower than conventional pulsing voltages to be used, resulting in less drain on the power source.

Because, preferably, no relatively long leads are used to connect the electrodes to the pulse generator (the pulse generator being preferably within the hermetically sealed capsule the base member of which mounts the electrode) the problems discussed above in relation to relatively long leads do not exist. The pacemaker of the present invention can therefore preferably be run at low voltages, resulting in extended lifetime.

The electrodes on the surface of the base member preferably are not implanted in the heart tissue. They preferably contact the surface of the heart, providing stimulation epicardially. This preferably overcomes the problems associated with surgical implantation of electrodes. If the pacemaker and electrodes should shift position, the recalibration to select other electrodes to provide stimulating/sensing functions to obtain the most clinically appropriate stimulation can be carried out. There will preferably be no need for surgery to relocate any electrodes.

A means for sensing physical activity of the patient is preferably provided in the pacemaker and means for adjusting the response of the pacemaker in dependence upon the physical activity of the patient. The pacemaker can thus respond to an increase in physical activity of the patient, for example, by increasing the frequency of pacing pulses to the heart. Physical activity is preferably sensed by a sensor placed on the diaphragm to monitor changes in breathing rate, depth, etc of the patient. The sensor is preferably an electrode which is placed on an opposite face of the hermetically sealed chamber to the base member mounting the sensing and pacing electrodes.

Cardiac pacing can therefore be determined to suit the physiological requirements of the patient. The apical stimulation provided by the pacemaker preferably allows for a good hemodynamic response in response to changes in physical activity.

Preferably, each electrode is formed by a pair of capacitive plates and a dielectric. Each electrode preferably comprises a first capacitive plate on the outer surface of the base member, a dielectric, which preferably comprises the base member itself, and a second capacitive plate on the inside surface of the base member, is within the pacemaker chamber/housing. The second plate is connected to the pulse generator means.

The employment of a capacitive construction for the electrodes preferably enables stimulation and/or sensing of cardiac tissue from within a hermetically sealed pacemaker, thereby eliminating any need for direct connection via a long lead or through the pacemaker housing walls thereby eliminating current leakage and fragile lead throughs requiring a hole in the pacemaker housing walls.

The pulsing and sensing electrodes are preferably arranged in a ring array formation on the base member.

Capacitive plates on the outer surface of the base member are preferably made from tissue compatible materials, such as carbon fibre or platinum black.

Preferably, where the pacemaker comprises a hermetically sealed housing, the housing has an outer peripheral layer that comprises tissue compatible material which is light weight and non-metallic/insulating material.

Where physical activity is sensed by a diaphragm sensing means, the diaphragm sensing means may be arranged to contact the diaphragm on its sternal region approximately below the sixth rib to approximately the junction between the underlining intercostal muscles and the diaphragm.

The diaphragm sensing means may sense sound levels generated by the diaphragm.

Preferably, the diaphragm sensing means senses electrical activity near the intercostal muscle junction.

The pacemaker is preferably provided with a control means in the form of a processing means for controlling the pulse generator.

The processing means may be arranged to receive electrical signals from the diaphragm sensing means and process the electrical signals to determine the desired heart rate.

Preferably the processing means is arranged to receive electrical signals from the diaphragm sensing means and process the electrical signals to produce signals indicative of the respiration rate of the diaphragm.

The processing means may be arranged to control the pulse generator to produce pulses indicative of the required heart beat rate based on the respiration rate sensed by the diaphragm sensing electrode.

Preferably the processing means comprises an electrical converter for converting a sensed signal from the diaphragm sensing means to a positive or negative going bias voltage which is arranged to alter the pulsing rate of the pulse generator.

The diaphragm sensing means may sense a current or voltage indicative of the respiration rate.

The processing means may comprise a diaphragm sensing system for receiving a sensed signal from the diaphragm sensing means.

The processing means may further comprise a CPU connected with the diaphragm sensing system.

The diaphragm sensing system can comprise an electrical transducer for converting signals received by the diaphragm sensing means to electrical signals compatible with the CPU.

The CPU preferably controls the pulse generator.

Preferably the CPU outputs data relating to the respiration rate.

The CPU may be programmed to control the pulse generator to produce pulses between a typical rate of 120 and 60 pulses per minute, i.e., produce a heart beat of 120 to 60 beats per minute depending on the sensed respiration rate.

The diaphragm sensing system may be arranged to sense through the diaphragm sensing means, changes in breathing rate, breathing depth or diaphragm velocity or changes in noise levels in the environment surrounding the diaphragm.

The processing means may comprise an output controller connected with the CPU and controlled by the CPU to control the pulse generator by converting signals from the CPU to a form compatible for controlling the pulse generator.

The processing means may comprise a telemetry means for receiving transmission signals from outside the pacemaker and communicating the signals to the CPU.

The telemetry means may comprise an antenna for receiving transmission signals.

The telemetry means may comprise a transmitter for transmitting signals through the antenna to an external receiver.

Preferably the CPU is arranged to be remote controlled by transmission signals received through the telemetry means.

Preferably the CPU can be instructed by the remote control to carry out self diagnostic steps which result in information which is arranged to be transmitted through the telemetry means to the external receiver.

It is preferred that the external receiver be a data processing means which is linked to a receiving antenna through a telemetry system.

Preferably the data processor comprises a keyboard which allows a user to control the data processor to send transmission signals to control the CPU of the pacemaker.

Preferably the pacemaker container is part hemispherical in shape with the first surface being a concave surface and the second surface being a convex surface.

The pacemaker may be arranged to be attached to the apex of a heart by an attachment device.

Preferably the attachment device comprises a body and a peripheral portion, the peripheral portion being arranged to be attached to the heart, the body portion being arranged to support the pacemaker.

From a second aspect, the present invention provides method of pacing the heart, comprising the step of providing pacing pulses to the apical area of the heart.

Pacing pulses are preferably provided by a plurality of electrodes positioned about the apical area of the heart. The method of this aspect of the present invention may be carried out by the pacemaker previously defined.

Preferably, the method includes the step of selecting between a number of available pacing/sensing electrodes to provide optimum cardiac output.

Preferably, the method further comprises the step of sensing the physical activity of the patient and adjusting the pacing of the heart in response to the degree of physical activity. This step preferably comprises sensing activity of the patients diaphragm.

The area around the intraventricular septum may be stimulates slightly before polarising the three walls of the ventricles, whereby to ensure a rigid septum as the ventricles are polarised.

From yet a further aspect, the present invention provides a heart pacemaker comprising a pacing electrode, pulse generator means for causing the electrode to provide cardiac stimulating pulses, a sensing means for sensing the physical activity of the patient and means for adjusting pacing of the heart by the electrode in response to variations in the physical activity of the patient.

Sensing means is preferably arranged to sense activity of the patient's diaphragm and is preferably an electrode adapted to contact the patient's diaphragm.

The pacemaker of this aspect of the invention may include any or all of the features of the pacemaker defined in relation to the first aspect of the invention above.

The present invention yet further provides a method of pacing a heart, comprising the steps of providing pacing pulses to the heart, sensing the physical activity of the patient, and varying the pacing of the heart in response to variations in the physical activity of the patient.

The method of this aspect of the invention preferably comprises the step of sensing the physical activity of the patient's diaphragm.

The method of this aspect of the invention may include any or all of the method steps of the first method aspect of the invention defined above.

The present invention yet further provides a heart pacemaker, comprising three or more pacing electrodes arranged to contact the heart to provide pacing pulses to the heart, pulse generator means for causing the pacing electrode to provide cardiac stimulating pulses and selection means for selecting one or more of the three or more electrodes to provide pacing pulses to the heart at any particular time, whereby one, some or all of the pacing electrodes may be used to provide stimulation as clinically appropriate.

The pacemaker of this aspect of the invention preferably also comprises a plurality of sensing electrodes, and the selection means is preferably arranged to select one or more of the sensing electrodes to provide sensing signals.

The pacemaker of this aspect of the invention may include any or all of the features of the aspects of the invention defined above.

The present invention yet further provides a method of pacing the heart, comprising placing three or more pacing electrodes in contact with the heart, and selecting one or more of the three electrodes to provide pacing pulses to the heart at any particular time, whereby one, some or all of the pacing electrodes may be used to provide stimulation as clinically appropriate.

The method of this aspect of the invention preferably comprises the further step of placing one or more sensing electrodes in contact with the heart to sense electrical activity of the heart, and selecting which of the sensing electrodes to use to provide sensing signals.

The method of this aspect of the invention may include any or all of the features of the aspects of the invention defined above.

The present invention yet further provides a heart pacemaker, comprising a housing containing a pulse generator means for causing pacing electrodes to provide cardiac stimulating pulses, the housing comprising a base member mounting at least one pacing electrode, the pacing electrode being constructed in the form of a capacitor and comprising a first capacitive plate on an outer surface of the base member, a dielectric and a second capacitive plate on the inner surface of the base member within the housing.

The dielectric is preferably formed by the base member itself.

The pacemaker of this aspect of the invention may include any or all of the features of the aspects of the invention previously defined.

The present invention yet further provides a heart pacemaker, comprising a hermetically sealed housing containing pulse generator means for causing pacing electrodes to provide cardiac stimulating pulses to the apical area of the heart, the housing comprising a base member mounting a plurality of pacing electrodes and being adapted to fit to the apex of the heart such that the pacing electrodes are positioned about the apex of the heart, the housing comprising a further member mounting a diaphragm sensing electrode adapted to contact the diaphragm and provide information relating to the physical activity of the patient, and means for adjusting pacing in response to variations in the physical activity of the patient.

The pacemaker of this aspect of the invention may include any or all of the features of the aspects as previously defined.

The present invention yet further provides a heart pacemaker, comprising a member mounting at least one electrode, the member being adapted such that the electrode may contact the surface of the heart but is not surgically implanted within heart tissue.

The pacemaker of this aspect of the invention may include any or all of the features of the aspects of the invention previously defined.

BRIEF DESCRIPTION OF THE DRAWINGS

Features and advantages of the present invention will become apparent from the following description of embodiments thereof, by way of example only, with reference to the accompanying drawings, in which.

The contents of copending PCT Application No. AU92/00219 are incorporated herein by way of reference.

DETAILED DESCRIPTION OF ILLUSTRATED EMBODIMENTS

Embodiments and features of that application may be combined with those of the present invention.

In particular, alternate or reverse prolarity pulsing of the electrodes may be applied.

Figure 1:
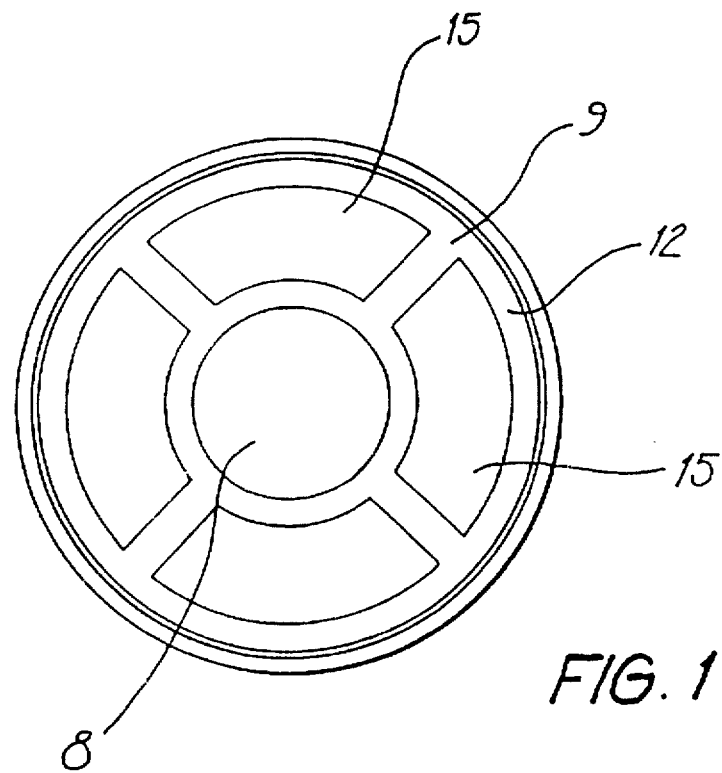
FIG. 1 is a back view of an implantable pacemaker in accordance with a preferred embodiment of the present invention.
Figure 2:
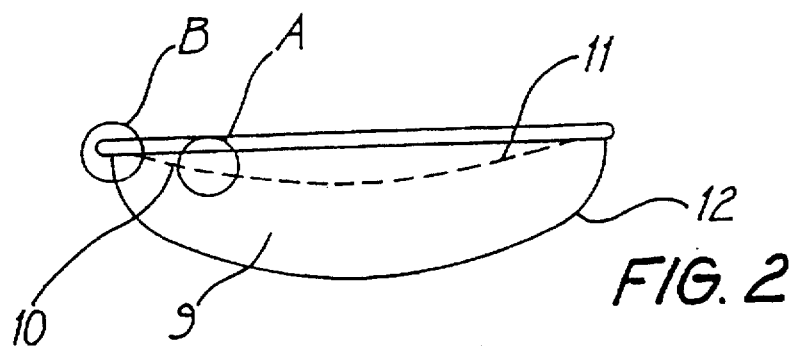
FIG. 2 is a side view of the pacemaker of FIG. 1.
Figure 3:
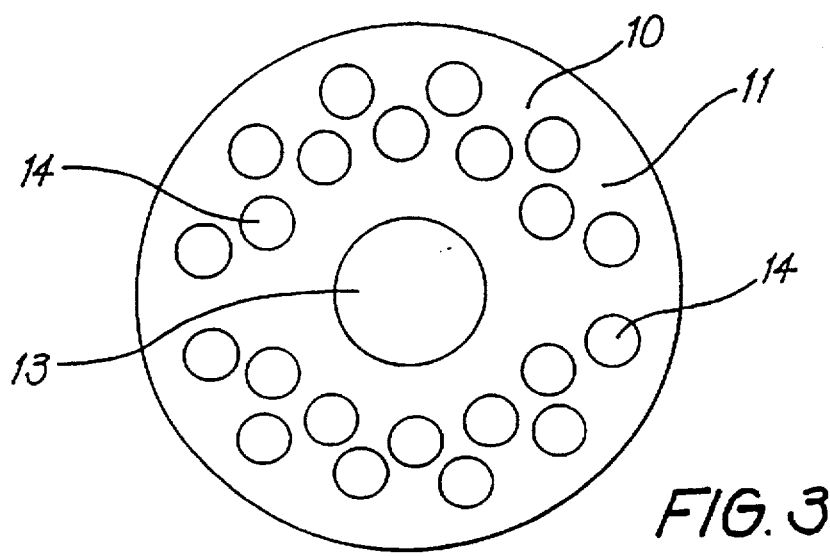
FIG. 3 is a front view of the pacemaker of FIG. 1.

The pacemaker shown in FIGS. 1 to 3 is a self contained hermetically sealed unit which may be made of a resilient plastics material or a ceramic material. The pacemaker according to this first embodiment is part hemispherical in shape or dish-shape and comprises a base member 10 having a concave surface 11 which forms the outer part of the surface a further housing member 9 having a convex surface 12 which opposes the concave surface 11. The two members 9 and 10 form a sealed container which houses electronic circuitry, comprising at least a pulse generator means, required to operate the pacemaker.

The concave surface 11 is shaped so that it will conform to the apical area of a heart at least to enable electrodes on the surface 11 to contact cardiac tissue on the apical area.

An array of pacing/sensing electrodes 14 are arranged on the surface 11 of the base member 10.

The electrodes 14 are substantially flush with the surface 11. They are arranged to contact heart tissue but not be implanted in the heart, to provide epicardial stimulation/sensing functions. A number of sensing and pacing electrodes 14 are provided and one, some or all of the electrodes may be selected for pacing and/or sensing, in order to provide optimum clinical pacing. An indifferent electrode 13 is also provided on the surface 11.

The sensing electrodes are positioned such that, when the pacemaker is fitted to the apex of the heart, they can distinguish between cardiac nerve impulses reaching the apex of the heart that may be caused by blockage of either left or right bundle branches or both.

Further, the pacing electrodes are mounted such that they are able to send pulses to the apex of the heart with such bias to the left or right of the apex or centrally around the intraventricular septum epicardium, or any combination thereof, so as to initiate a desired uniform spread of depolarisation wave through the heart.

Sensing means, in the form of diaphragm contacting electrodes 15, are provided on the surface 9 of member 12 of the pacemaker. These electrodes 15 are arranged to contact the diaphragm, when the pacemaker is in position, on its sternal region approximately below the sixth rib and proximate the junction between the underlying intercostal muscles and the diaphragm. With the pacemaker located in this position, the amount of relative movement between the heart and the diaphragm is minimised. These electrodes 15, are used to sense variations in the physical activity of the patient by detecting changes in depth, rate, etc of breathing. An indifferent electrode 8 is also provided on the surface 12.

The pacing and sensing electrodes 14 are not distinguished in FIG. 3. It is preferred that the pacing and sensing electrodes are separated, to avoid polarisation effects having affect on sensing of electrical activity of the heart. The same electrode may be used for both functions, however, as is conventional.

Figure 6:
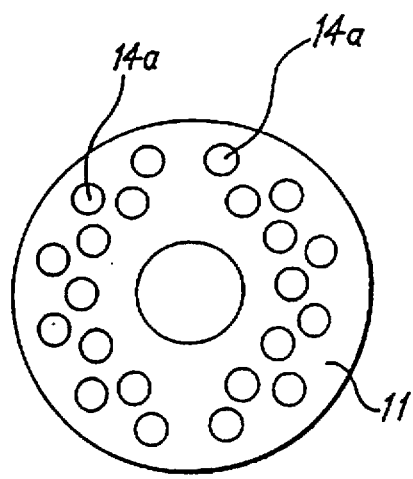
FIG. 6 is a further front view of the pacemaker of FIG. 1.
Figure 7:
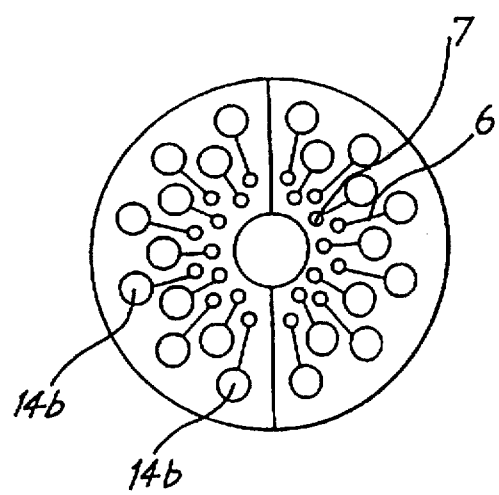
FIG. 7 is a view of the inner surface, inside the pacemaker, of a base member of the pacemaker of FIG. 1.

The construction of the electrodes 14 will now be described with reference to FIGS. 5 through 7.

Figure 5:
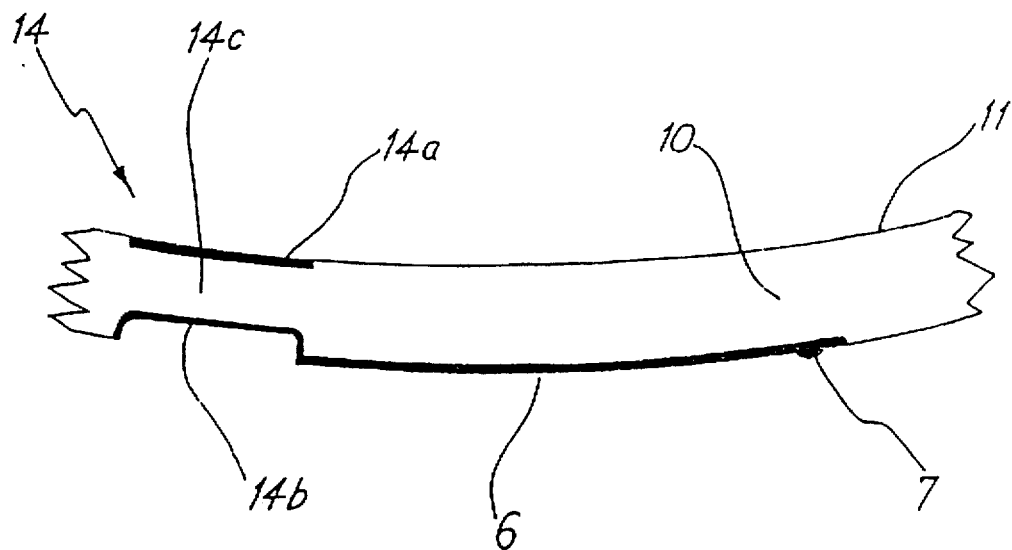
FIG. 5 is a section through a portion of a base member of the pacemaker of FIG. 1.

FIG. 5 is a sectional view of portion A of FIG. 2, being a section through base member 10. The section shows a sectional view through one electrode arrangement. Each electrode 14 comprises a first capacitive plate 14a on the outer surface 11 of base member 10, and a second capacitive plate 14b on the inside surface of the base member 10 within the pacemaker container. The capacitive arrangement is completed by dielectric 14c, in between capacitive plates 14a and 14b, and being formed by the base member 10 material. Each outer capacitive plate 14a is made of physically compatible conductive material, for example micro porous platinum black. Each inner capacitive plate 14b may be made of gold or platinum or other suitable metal deposited upon the inner surface of the base member 10. Base member 10 is of a material having a high dielectric constant and being physiologically compatible ceramic or other suitable material. The outer capacitive plate 14a may be made of any other suitable ptc conductive material deposited upon the outside surface 11.

Conductive printed wiring 6 is provided on the internal surface of the base member 10 to connect the inner capacitive plate 14b to a connecting join 7 which is connected to a wire connecting the electrode 14 to pacemaker circuitry including a pulse generator.

The use of capacitive electrodes 14 means that the pacemaker can be completely hermetically sealed against the external environment and there is no need for holes through the pacemaker body to provide connections for electrodes.

Electrodes have the further advantage that they are constituted, on the outer surface of the base member 10, by a flat plate 14a which does not require implantation into heart tissue. If the pacemaker should shift position, such that electrodes presently being used for pacing and sensing do not provide optimum cardiac stimulation, different electrodes can be selected on recalibration to provide optimum pacing.

The electrodes 13, 8 and 15 of the pacemaker also have similar capacitive constructions to the electrodes 14.

Figure 8:
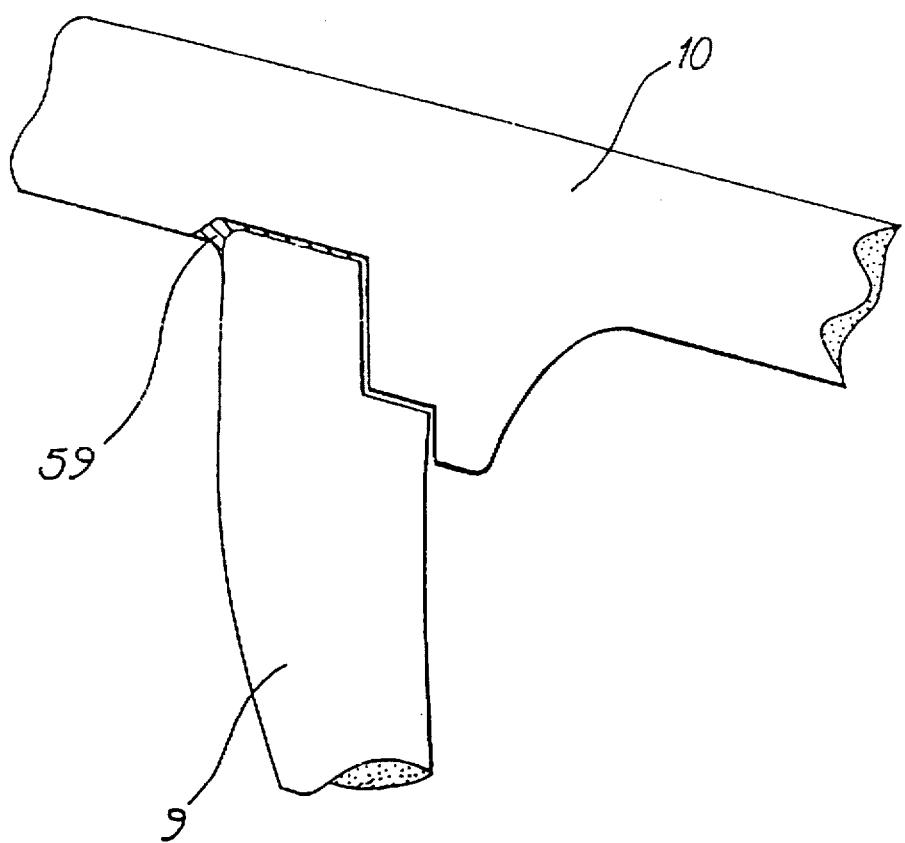
FIG. 8 is a detail of a join between front and back portions of a housing of the pacemaker of FIG. 1.

FIG. 8 shows a detail (B from FIG. 2) of the joint of the base member 10 with further housing member 9 of the pacemaker. Surplus metal 59 between the back 9 and base member 10 is fused by laser beam welding or other suitable means to form a continuous hermetic metal ring seal 59. This ring seal also provides an electrical return or loop in order to electrically protect the pacemaker electronics from the adverse effects of interference from stray and undesirable random electrical fields.

Figure 4:
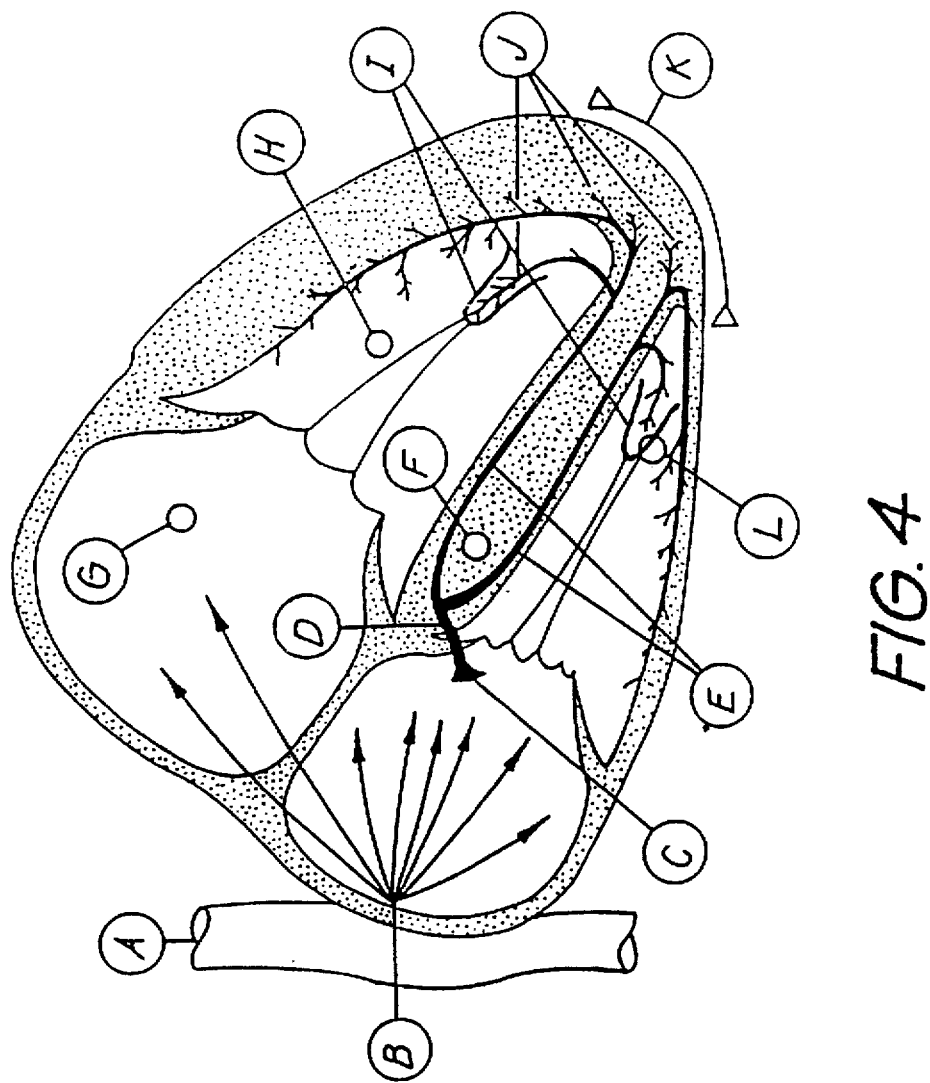
FIG. 4 is a schematic cross-sectional diagram through a heart to illustrate major cardiac features and the site where the pacemaker in accordance with the present invention is preferably positioned.

FIG. 4 is a diagram illustrating major features of the heart. The reference letters on the diagram indicate the following features:

A. Superior vena cava;
B. SA node;
C. AV node;
D. Bundle of His;
E. Bundle branches;
F. Septum;
G. Left atrium;
H. Left ventricle;
I. Papillary muscle;
J. Purkinje fibres;
K. Apical pacemaker electrode site;
L. Conventional pacemaker electrode site.

The normal electrical pathway goes as follows:

B→C→D→E→J.

The pacemaker in accordance with the present invention is arranged to be positioned at site K, at the apical area of the heart where the free walls of the left and right ventricles meet the intraventricular septum. The pacemaker is positioned so that the electrodes 14, 13 contact the apical surface of the heart and the electrodes 15, 8 contact the diaphragm. The electrodes 15, 8 are arranged to contact the diaphragm on its sternal region approximately below the sixth rib and proximate the junction between the underlying intercostal muscles and the diaphragm. With the pacemaker located in this position, the amount of relative movement between the heart and the diaphragm is minimised.

Pacing the apical area of the heart by pacing electrodes 14 allows the septum, and free walls of the left atrium and left ventricle to be stimulated substantially simultaneously to enable synchronous stimulation of the ventricles. This preferably overcomes problems with conventional pacing as discussed in the preamble of the specification.

In an alternative embodiment, stimulation may be arranged such that the septum is stimulated slightly before the free walls of the ventricles, to enable the ventricles to be polarised from a solid septum base.

Figure 9:
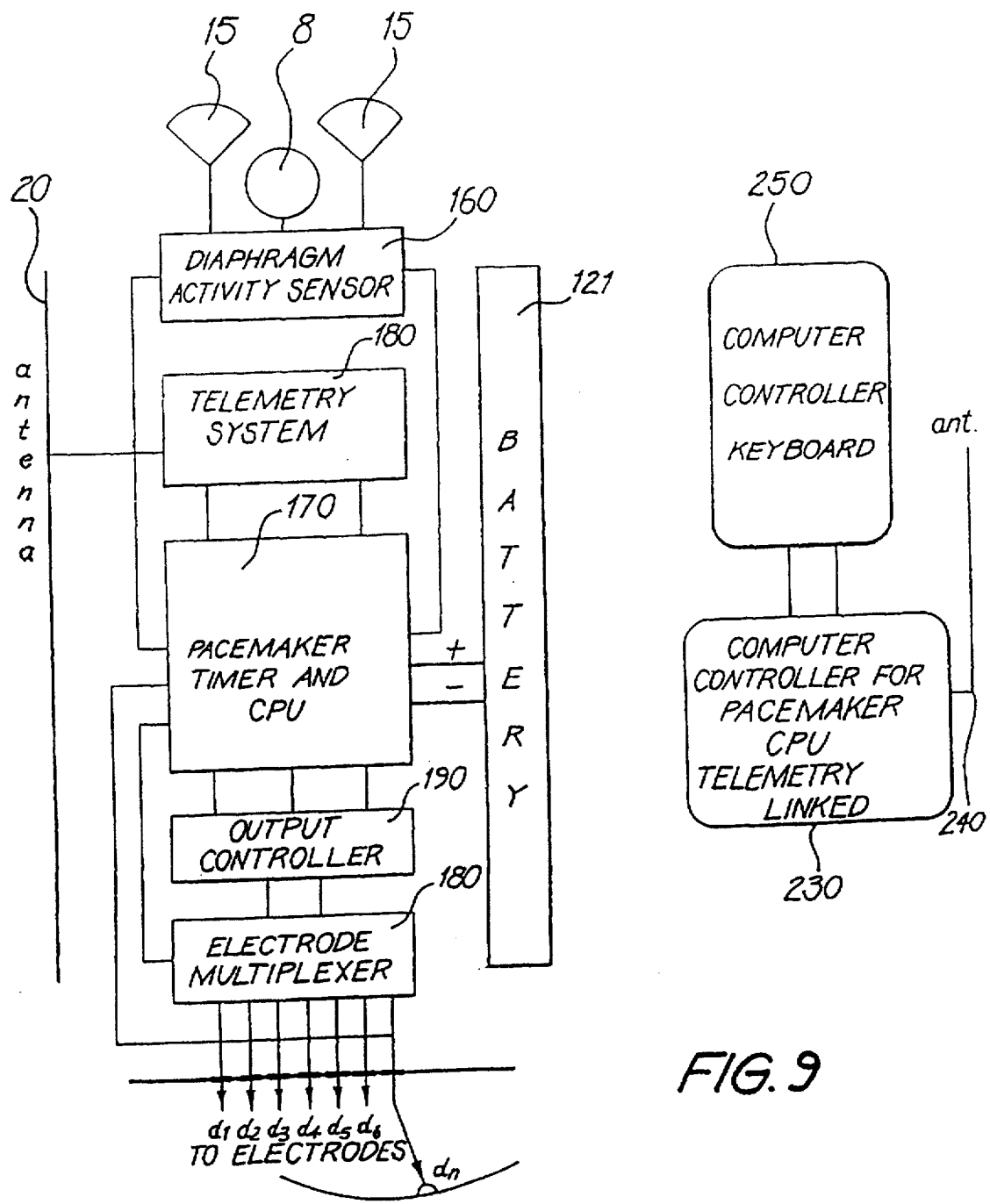
FIG. 9 is a schematic block circuit diagram showing electronic circuitry for use with a pacemaker in accordance with an embodiment of the present invention.

Referring to FIG. 9 of the present invention, the electrical circuitry required to operate the pacemaker comprises diaphragm sensing electrodes 15 and indifferent electrode 8 which are connected through the external surface of the convex surface 12 to a diaphragm activity sensor 160 located inside the pacemaker container.

The diaphragm activity sensor 160 is connected to a CPU 170 which in turn is connected to a telemetry transmitter receiver 180 and an output controller 190 for calibration. The output controller 190 is connected to an electrode multiplexer 120 and a battery 121 provides a power supply for the CPU and all other components of the electrical system.

The telemetry transmitter/receiver 180 is connected to an antenna 220 which allows transmittal of signals between the pacemaker and a computer controller 230 connected to a remote antenna 240.

In use, the pacemaker is mounted on the apex of a heart so that the electrodes 13 and 14 are in contact with the apical area of the heart. The electrodes are used for pacing the apical area of the heart and are also used for sensing their electrical activity.

The electrodes 15 sense the electrical activity of the diaphragm near the intercostal muscle junction and the electrical activity in the muscles of the intercostal muscles and the sensed signals are transferred to the diaphragm activity sensor 160.

The diaphragm activity sensor 160 converts the receive signals to a form which is compatible with the CPU 170. The CPU then, after receiving the converted signals from the diaphragm activity sensor 160, operates a program to determine the respiration rate based on the information received from the diaphragm sensing electrodes 15. Once the respiration rate has been calculated, a desired heart beat rate is determined and a signal is sent from the pacemaker and CPU 170 to operate the electrodes 14 to provide pulses to the apical area of the heart to make the heart beat in accordance with the sensed respiration rate.

A timer circuit connected to the pulse generator is controlled by the CPU to produce pulses separated by the desired time interval (the pulse generator means, timer and other conventional circuitry for operating a pacemaker are contained within block 170).

The pulse generator outputs pulses which are filtered by an output circuit controlled by the CPU and are then fed to each of the electrodes. Sensing electrodes 14 also sense cardiac activity and provide information to the CPU for control of pacing electrodes 14. This is done in conventional pacemakers.

In operation, the electrical activity of the diaphragm near the intercostal muscle junction as sensed by the electrodes 15 and the diaphragm activity sensor 160 converts the electrical activity into a positive going or negative going bias voltage which in turn alters the pacing rate of the pacemaker depending on the physiological requirements of the pacemaker patient. When the patients physical activity increases significantly their respiration rate naturally increases with their need to increase cardiac output which in turn also increases the signal voltage applied to the sensing circuit via the electrodes of the pacemaker, which in turn increases pacing rate by a predetermined amount set by an algorithm programmed into its CPU to say 120 beats per minute. Similarly, when the patient is at rest, their resting respiration rate is low. The pacemaker rate will follow and drop to a predetermined minimum, of say, 60 beats per minute to match the decreased requirement of cardiac output.

It follows therefore, that the breathing characteristics of a patient using this epimyocardial pacemaker determine the pacing rate and hence cardiac output by sensing the changes in breathing rate, changes in breathing depth or diaphragm velocity, matching cardiac output to suit their physiological state.

Selection of which sensing/pacing electrodes are to be used is made by use of output controller 190 and electrode multiplexer 120. The output controller 190 is controlled, by CPU 170, to select particular outputs of the electrode multiplexer 120 to be used for pacing/sensing. Selection will usually be made on calibration and recalibration, by telemetry under control of a physician, although it is an option that computer control of the pacemaker itself could be sophisticated enough to enable selection to be made automatically.

With the electronic circuitry shown in FIG. 9, the respiration rate and depth of breathing of the patient together with the determination of the physician, produces a stimulating rate for the pacemaker which is consistent with the physiological requirements of the patient. The pacemaker is linked by telemetry to a controller for initial setting of patient requirements, and for periodic re-setting. These initial settings can be input into the computer controller through a computer controller keyboard 250. A signal is transmitted through the antenna 210 and is received by the antenna 220 in the pacemaker which through the telemetry system 180 is transferred to the CPU 170 which then operates the pacemaker according to the instructions received. It is preferred that the electrical circuitry of the pacemaker be designed on a single integrated circuit chip. It is conventional to use telemetry to set, monitor and re-set pacemakers. Normally, pulse width, height, voltage and other parameters are set by using telemetry under the control of a physician. In the case of the present invention, the physician will also be able to determine which electrodes should be used for sensing and/or pacing and to set the output control 190 and multiplexer 120, via CPU 170, to ensure that those electrodes are used. If the pacemaker should shift position, or if further diagnosis should establish that it would be better to use other electrodes, then another selection process can be carried out to select other electrodes. There will be no need for surgery to relocate the position of any electrodes.

Preferably the battery incorporates a lithium pacemaker battery of proven reliability such as model 8 711 manufactured by Wilson Greatback Limited of Clarence, N.Y. U.S.A.

Preferably the pacemaker CPU receives, compares, interprets and sends specific data bout patient related functions and responds to signals from the cardiologist via the telemetry system, in the diaphragm sensing system, from the internal CPU algorithms and to and from the cardiologist in response to changing patient conditions. This enables diagnosis and correct setting of limits for administration of pacemaker treatment for the patient condition observed.

Desirably, the diaphragm sensing electrodes are of a low current density type. The CPU 230 may be a standard IBM type 486DX2 running at 50 megahertz equipped with 32 Mb RAM, 330 Mb hard disk super VGA video and display, BIOS shadowing, standard floppies, MSDOS5, MS Mouse, 256K cache and specially written software.

Preferably the cardiologist is presented with all the necessary patient information on the screen of his computer controller as relayed from the pacemaker CPU 170 via the telemetry system.

Figure 10:
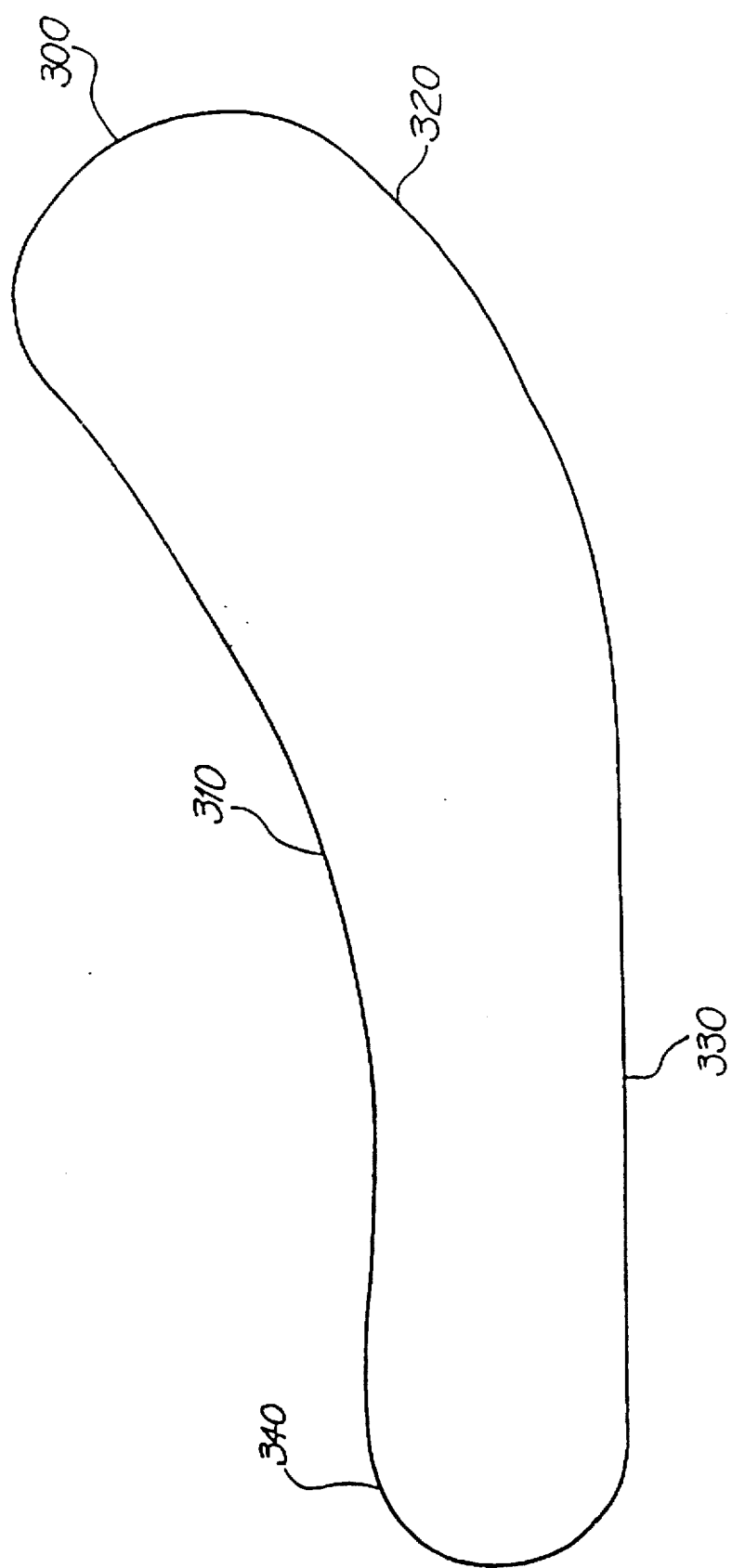
FIG. 10 is a side view of a pacemaker in accordance with an alternative embodiment of the present invention.
Figure 11:
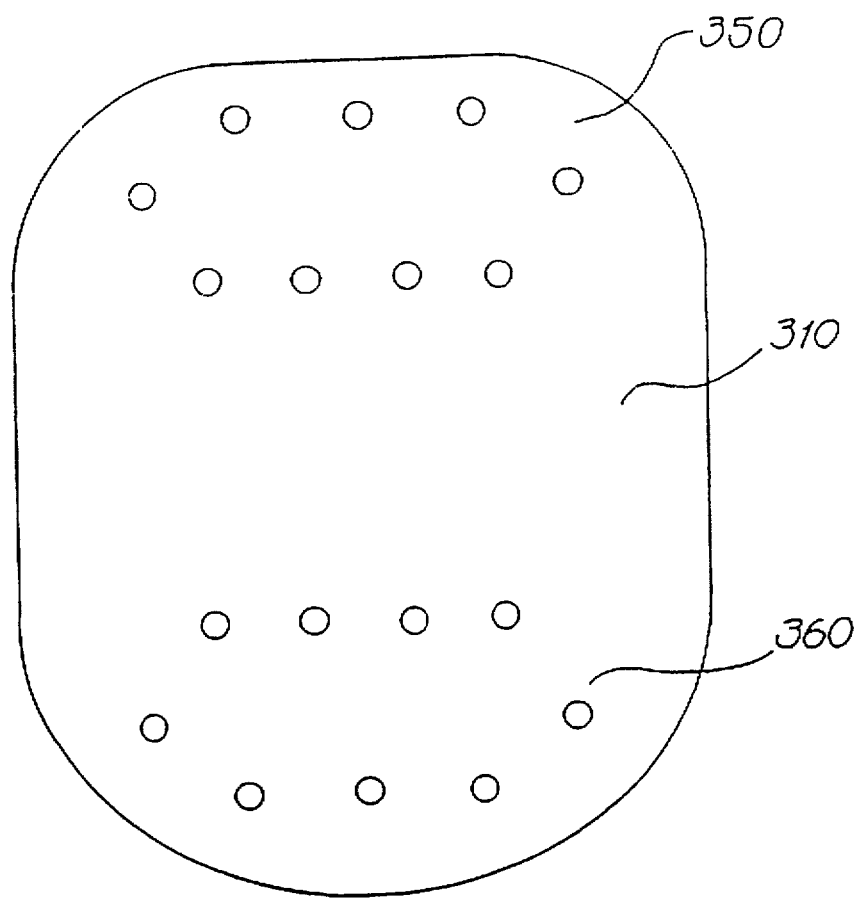
FIG. 11 is a front view of the pacemaker of FIG. 10.

According to another embodiment of the present invention as shown in FIGS. 10 and 11, the pacemaker has an irregular shape. As shown in more detail in FIG. 4, the pacemaker comprises a container 300 with an upper concave surface 310 which is arranged to abut the apex of the heart and a right side convex surface 320 which at its lower most point extends into a rectilinear surface 330 which terminates in an arcuate surface 340 which is almost semicircular and joins with the concave surface 310. The surfaces 320 and 330 are arranged to abut the upper surface of the diaphragm.

As shown in FIG. 11, the concave surface 31 is provided with two arrays of electrodes 350 and 360 which are arranged to contact the apical area of the heart. The array of electrodes allows a stimulating pulse to be transmitted from any one of the electrodes (as in the previous embodiment) thus, eliminating the problem of desensitizing a particular area or damaging a particular area of the heart due to repeated use of a single electrode. The array of electrodes is flush or almost flush with the concave surface 31. This pacemaker may contain circuitry as described above and the electrodes are also of capacitive construction. Diaphragm sensing electrodes are also provided.

A pacemaker in accordance with embodiments of the present invention may be attached to the heart using an attachment device as shown in FIG. 2 of copending PCT application AU92/00219.

I claim:

1. A heart pacemaker, comprising a housing containing a pulse generator means for providing cardiac stimulating pulses, the housing comprising a base member mounting at least one pacing electrode, the pacing electrode being constructed in the form of a capacitor and comprising a first capacitive plate on an outer surface of the base member, a dielectric and a second capacitive plate on the inner surface of the base member within the housing, said pulse generator means providing said pulses to said pacing electrode.

2. A heart pacemaker in accordance with claim 1, the dielectric being formed by the base member.

3. A heart pacemaker in accordance with claim 1, the base member being arranged to fit to the apex of the heart such that the pacing electrode is able to provide stimulation to the apex of the heart, and wherein the pulse generator means causes the electrode to provide cardiac stimulating pulses to the apical area.

4. A heart pacemaker in accordance with claim 3, wherein a plurality of sensing electrodes are mounted on the base member for sensing electrical activity of the heart and for providing the sensed electrical activity to the pulse generator means, the plurality of sensing electrodes being placed so as to be positioned about the apical area of the heart.

5. A heart pacemaker in accordance with claim 4, the sensing and pacing electrodes being arranged in a ring array on the surface of the base member.

6. An electrode arrangement for a heart pacemaker, comprising a base member mounting a plurality of pairs of capacitive plates, one capacitive plate in each pair being arranged on an outer surface of the base member for contact with heart tissue, and the other capacitive plate in each pair being mounted on the inner surface of the base member opposite the first capacitive plate, whereby to form a capacitive electrode array.

* * * * *